United States Patent [19]

Hartmann et al.

[11] Patent Number: 4,908,477

[45] Date of Patent: Mar. 13, 1990

[54] REMOVAL OF ORGANIC IODINE COMPOUNDS FROM CARBONYLATION PRODUCTS OF METHANOL METHYL ACETATE AND DIMETHYL ETHER

[75] Inventors: Horst Hartmann, Boehl-Iggelheim; Waldhelm Hochstein, Freinsheim; Gerd Kaibel, Lampertheim; Franz-Josef Mueller, Wachenheim, all of Fed. Rep. of Germany

[73] Assignee: BASF Aktiengesellschaft, Ludwigshafen, Fed. Rep. of Germany

[21] Appl. No.: 23,990

[22] Filed: Mar. 9, 1987

Related U.S. Application Data

[63] Continuation of Ser. No. 348,199, Feb. 12, 1982, abandoned.

[30] Foreign Application Priority Data

Feb. 28, 1981 [DE] Fed Rep of Germany ...... 3107731

[51] Int. Cl.[4] ...................... C07C 51/48; C07C 45/80; C07C 67/58; C07C 53/08
[52] U.S. Cl. .................................... 560/248; 560/232; 562/517; 562/519; 562/608; 562/891; 562/898; 568/485; 568/487; 568/492; 568/594; 568/902; 568/909; 568/913
[58] Field of Search ............... 562/519, 608, 577, 891, 562/898; 348/199; 560/248, 232; 260/549; 568/492, 487, 594, 913, 902, 909, 485

[56] References Cited

U.S. PATENT DOCUMENTS

| 3,616,271 | 10/1971 | Copelin | 568/492 |
| 4,241,219 | 12/1980 | Wan | 560/232 |
| 4,246,195 | 1/1981 | Szusi | 568/492 |
| 4,255,591 | 3/1981 | Makin | 562/517 |

FOREIGN PATENT DOCUMENTS 2940751 4/1980 Fed. Rep. of Germany .
3045105 7/1982 Fed. Rep. of Germany .

OTHER PUBLICATIONS

Mellan, Ibert, Industrial Solvents, Second Edition, Book Division, Reinhold Publishing Corp., N.Y., 1950, p. 4.
W. West et al, Journal Amer. Chem. Soc., 62, 3021–6, 1940 (CA. 35:3868).

*Primary Examiner*—Vivian Garner
*Attorney, Agent, or Firm*—Keil & Weinkauf

[57] ABSTRACT

Organic iodine compounds are separated from carbonylation products of methanol, methyl acetate and dimethyl ether and from mixtures of such carbonylation products by a process wherein the iodine compounds are removed by liquid phase extraction with a non-aromatic hydrocarbon.

5 Claims, No Drawings

REMOVAL OF ORGANIC IODINE COMPOUNDS FROM CARBONYLATION PRODUCTS OF METHANOL METHYL ACETATE AND DIMETHYL ETHER

This application is a continuation of application Ser. No. 348,199, filed on Feb. 12, 1982, now abandoned.

The present invention relates to a novel process for removing organic iodine compounds such as, in particular, methyl iodide, from carbonylation products of methanol, methyl acetate and dimethyl ether and from mixtures of such carbonylation products.

It is generally known that methanol, methyl acetate and dimethyl ether can react with carbon monoxide or with carbon monoxide and hydrogen in the presence of carbonyl-forming metals, chiefly those of group VIII of the periodic table, in many ways, to give various products.

These reactions are usually described by the generic term carbonylation. Specifically, these reactions are, inter alia, carbonylation (in the narrower sense) of methanol or dimethyl ether with, inter alia, a Co, Ni or Rh catalyst to give a mixture substantially consisting of methanol, acetic acid and methyl acetate, carbonylation (in the narrower sense) of methyl acetate with, inter alia, a Co, Ni or Rh catalyst to give a mixture substantially consisting of methyl acetate and acetic anhydride, homologization of methanol and dimethyl ether with $CO/H_2$ in the presence of, inter alia, a Co, Ni or Rh catalyst to give, depending on the reaction conditions, a mixture which, in addition to methanol, essentially contains acetaldehyde, ethanol, methyl acetate, acetaldehyde dimethyl acetal and water, and homologization of methyl acetate with $CO/H_2$ in the presence of, inter alia, a Co, Ni or Rh catalyst to give, depending on the reaction conditions, a mixture substantially consisting of ethylidene diacetate, vinyl acetate, methyl acetate, ethyl acetate, water and methanol.

A large number of embodiments have been disclosed or are conceivable for all of these processes, so that a correspondingly large number of reaction mixtures of varying qualitative and quantitative composition is obtained. However, the common factor of most variants of these carbonylation reactions is that they are carried out in the presence of iodides so that the reaction mixtures always contain significant amounts of organic iodine compounds, such as, in particular, methyl iodide.

These organic iodine compounds are extremely difficult to remove from the remaining organic components of the carbonylation mixtures.

Fractionation, if possible at all in spite of the many types of azeotrope formation, entails uneconomically high separation costs, and chemical methods such as oxidation, reduction or treatment with alkali cannot be used because of the sensitivity of some carbonylation products, quite apart from the fact that they are technologically involved and in most cases only replace a difficult separation problem by one which is only in principle less difficult.

German Laid-Open Application DOS 2,940,751, for example, discloses, the removal of methyl iodide from carbonylation products of methyl acetate by reaction with alkali metal acetates, alkali metal iodides being obtained. As, however, this reaction takes place only at elevated temperatures, it must be carried out under superatmospheric pressure and the iodine salts must then be separated off. These measures and the subsequent recycling of the iodides to the process circulation are, however, technologically expensive and unsatisfactory and, in particular, cannot harmoniously be included in a continuous procedure. Finally, if water is present as a component of the reaction mixture, this method of removal of iodine is virtually impossible.

Prior Patent Application 3,045,105.9 which became German Laid-Open Specification No. 3,045,105, which is equivalent to U.S. Pat. No. 4,383,894 discloses a process in which acetaldehyde is separated off from organic iodine compounds, such as, in particular, methyl iodide, by distilling off the acetaldehyde as an azeotrope with a hydrocarbon having a boiling point of 25°-55° C. under atmospheric pressure. In this case, the organic iodine compounds remain in the distillation residue and the acetaldehyde can be obtained from the azeotrope in a conventional manner by extraction with water and isolation by distillation from the extract phase.

Prior Federal Republic of Germany Patent Application 3,045,105.9 European published specification No. 0,053,249, which was published on June 9, 1982, and which is equivalent to U.S. application Ser. No. 315,726, which was filed on Oct. 28, 1981, now U.S. Pat. No. 4,399,001 discloses a process in which organic iodine compounds can be isolated from acetaldehyde-free carbonylation mixtures, for example those which have been freed from acetaldehyde by the above process, by removal with the aid of the same hydrocarbons by azeotropic distillation.

It is an object of the invention to remove methyl iodide and other organic iodine compounds from reaction products of the carbonylation of methanol, methyl acetate and dimethyl ether and from mixtures of such carbonylation products in another simple and economical manner.

We have found that this object is achieved and that methyl iodide and other organic iodine compounds can be separated off in an advantageous manner from reaction products of the carbonylation of methanol, methyl acetate and dimethyl ether or from mixtures of such carbonylation products if the iodine compounds are removed by liquid phase extraction with a non-aromatic hydrocarbon.

Surprisingly, the process according to the invention can be used not only on certain carbonylation products of methanol, methyl acetate and dimethyl ether but also on any mixtures which may be obtained in these reactions. Further working up of such mixtures no longer presents the problem of removal of iodine and can therefore be carried out in any desired manner.

About 100-3,000 g of the hydrocarbon are used per gram of iodine compounds, chiefly methyl iodide, in the extraction process according to the invention. Suitable non-aromatic hydrocarbons are all those which are liquid under the extraction conditions. Straight-chain or branched $C_4-C_{14}$-alkanes, mono-, bi- and tricyclic cycloalkanes having 5 or 6 carbon atoms per ring and mixtures of these hydrocarbons are therefore suitable. Examples of such hydrocarbons are isopentane, 2,2,4-trimethylpentane, n-octane, n-nonane, n-decane, cyclopentane, cyclohexane and decahydronaphthalene.

The hydrocarbons conforming to the above definitions generally have a markedly selective dissolving power for the organic iodine compounds, especially for methyl iodide, which chiefly occurs in the carbonylation mixtures in question. In contrast, the more polar the other components are, the less they pass into the extract phase. Thus, virtually no water, acetic acid, ethanol, acetaldehyde or methanol is extracted, whilst small amounts of dimethyl ether, methyl acetate and acetaldehyde dimethyl acetal can also pass into the extract phase. The efficiency of the extraction can frequently be improved by adding about 20–200% by weight of water, based on the product or product mixture to be extracted.

The extraction is preferably carried out under atmospheric pressure at from 0° to 30° C. Slightly increased pressure, for example not more than 4 bar, may be necessary if a $C_4$-hydrocarbon such as butane or isobutane is used. Moreover, the pressure is increased, for example to not more than 10 bar, if the extraction is carried out at higher temperatures, for example at not more than 70°–80° C.

The extraction can be carried out batchwise or, preferably, continuously in any conventional apparatuses, for example in a mixer/settler apparatus or extraction column of any desired construction, the hydrocarbon being passed from the bottom upwards, in countercurrent to the carbonylation mixture. If a single extraction operation does not lead to the desired removal of organic iodine compounds, several, for example not more than 10, extraction stages can be performed in series.

The extract phase is worked up by distilling off the small amounts of iodine compounds from the extracting agent and is advantageously recycled to the carbonylation stage. Extracting agent which thereby passes into the distillate and any carbonylation products also extracted can likewise be recycled to the carbonylation stage since they cause no trouble there.

Furthermore, the iodine can be removed in any desired chemical manner, for example by treatment with alkali metals or alkali metal hydroxide solutions and subsequent separation of the iodides from the inert hydrocarbons.

The removal of residues of extracting agent from the raffinate phase is simple if, as is always possible, an extracting agent is chosen which has a boiling point sufficiently different from the components of the raffinate phase or from secondary products thereof, so that separation by distillation can easily be carried out.

In principle, the process according to the invention is independent of the conditions under which, and the aim with which, carbonylation has been carried out, if iodine compounds have been used at all as activators in the carbonylation catalyst system, as is the case for most of the syntheses of this type carried out industrially. It is therefore not necessary to state specifically the various reaction conditions for the above carbonylation reaction variants.

The process according to the invention enables the iodine content of the carbonylation products or of mixtures thereof to be reduced from about 1,000–10,000 ppm to 0.01–20 ppm in an extremely simple manner.

EXAMPLES 1–12

In each case m g of a carbonylation product or of a mixture of such products with a methyl ioddide content of p ppm were extracted by shaking n times with in each case 100 g of a hydrocarbon, as the extracting agent, at T° C. The product losses resulting from the extraction and the methyl iodide content after the nth extraction stage were then determined. The methyl iodide content was determined by gas chromatography.

The details of these experiments and their results can be found in the table.

| Example No. | Product (mixture) Nature | P to be extracted Amount m (g) | P to be extracted $CH_3I$ content p (ppm) | Extracting agent | Extraction stages n | Temperature °C. | Raffinate phase Loss of P (g) | Raffinate phase $CH_3I$ content (ppm) |
|---|---|---|---|---|---|---|---|---|
| 1 | Acetic acid | 100 | 5,000 | Decahydronaphthalene | 5 | 25 | 3 | 86 |
| 2 | Acetic acid<br>Water | 75<br>50 | 2,900 | Decahydronaphthalene | 5 | 25 | 0.3 | 0.2 |
| 3 | Acetic acid<br>Methyl acetate | 67<br>33 | 4,700 | Decahydronaphthalene | 4 | 25 | 3<br>3 | 210 |
| 4 | Acetic acid<br>Methyl acetate<br>Water | 50<br>50<br>50 | 3,400 | Decahydronaphthalene | 5 | 25 | 0.2<br>2 | 0.1 |
| 5 | Acetic anhydride<br>Methyl acetate | 50<br>50 | 3,900 | Decahydronaphthalene | 5 | 25 | 1<br>2 | 15 |
| 6 | Acetic anhydride<br>Methyl acetate<br>Ethylidene diacetate | 33<br>33<br>33 | 6,500 | Decahydronaphthalene | 5 | 25 | 0.2<br>2<br>1.5 | 63 |
| 7 | Acetaldehyde<br>Water | 100<br>100 | 150 | Isopentane | 3 | 10 | 2 | 0.2 |
| 8 | Acetaldehyde<br>Water | 100<br>100 | 280 | 1,2,4-Trimethylpentane | 3 | 18 | 2 | 0.6 |
| 9 | Acetaldehyde<br>Water | 100<br>100 | 280 | n-Nonane | 3 | 18 | 1.5 | 0.8 |
| 10 | Acetaldehyde<br>Water | 100<br>100 | 280 | n-Octane | 3 | 18 | 1.5 | 0.8 |
| 11 | Acetaldehyde<br>Water | 100<br>100 | 280 | Decahydronaphthalene | 3 | 18 | 1 | 0.6 |
| 12 | Acetaldehyde<br>Water | 100<br>100 | 280 | n-Decane | 3 | 18 | 1.5 | 0.5 |

EXAMPLE 13

500 g per hour of a carbonylation mixture were extracted in countercurrent with 250 g per hour of n-decane in a continuously operated 3-stage mixer/settler apparatus at 20° C.

The carbonylation mixture was prepared by carbonylation of methanol with synthesis gas ($CO:H_2 = 1.3:1$) in the presence of cobalt carbonyl, as the catalyst, and sodium iodide, as the activator, at 185° C. and 300 bar. After oxidative decobalting, the liquid constituents were diluted with water, after which the mixture had the following composition: 50% of water (% by weight, as in the following), 5% of acetaldehyde, 9% of acetaldehyde dimethyl acetal, 8% of methyl acetate, 26% of methanol and 2% of ethanol. This mixture contained 120 ppm of methyl iodide.

After the extraction, the raffinate phase still contained only 0.4 ppm of methyl iodide. The losses of carbonylation products resulting from the extraction were about 1-2% of methyl acetate and about 2-3% of acetaldehyde dimethyl acetal.

We claim:

1. A process for purifying a mixture of liquid carbonylation products formed in the carbonylation of methanol, methylacetate and/or dimethyl ether in the presence of iodides by removing methyl iodide from said products, which process comprises: passing a non-aromatic hydrocarbon of 4–14 carbon atoms in countercurrent direction through the liquid carbonylation mixture to extract methyl iodide from the mixture of carbonylation products in from 1 to 10 extraction stages and thus substantially lowering the amount of methyl iodide in such products.

2. The process of claim 1, wherein the extraction is carried out in the presence of from about 20 to 200% by weight of water based on the product to be extracted.

3. The process of claim 1, wherein the non-aromatic hydrocarbon is isopentane, 2,2,4-trimethylpentane, n-octane, n-nonane, n-decane, cyclopentane, cyclohexane or decahydronaphthalene.

4. The process of claim 1, wherein the non-aromatic hydrocarbon is a straight-chained or branched-chained $C_4$–$C_{14}$-alkane or a mono-, bi- or tricyclic cycloalkane having 5 or 6 carbon atoms per ring or mixtures of said non-aromatic hydrocarbons.

5. The process of claim 4, wherein the extraction is carried out in the presence of from about 20 to 200% by weight of water based on the product to be extracted.

* * * * *